(12) United States Patent
Green et al.

(10) Patent No.: US 6,911,431 B1
(45) Date of Patent: *Jun. 28, 2005

(54) PHARMACEUTICAL ANGIOSTATIC DIPEPTIDE COMPOSITIONS AND METHODS OF USE THEREOF

(75) Inventors: Lawrence R. Green, Tacoma, WA (US); John W. Blasecki, Woodinville, WA (US)

(73) Assignee: Melmotte, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/506,430

(22) Filed: Feb. 17, 2000

Related U.S. Application Data

(63) Continuation of application No. 09/260,190, filed on Mar. 1, 1999, now Pat. No. 6,096,713, which is a continuation of application No. 08/614,764, filed on Mar. 13, 1996, now Pat. No. 5,902,790, which is a continuation of application No. 08/538,701, filed on Oct. 3, 1995, now abandoned, which is a continuation-in-part of application No. 08/401,653, filed on Mar. 9, 1995, now abandoned, which is a continuation-in-part of application No. 08/278,463, filed on Jul. 21, 1994, now abandoned, and a continuation-in-part of application No. 08/370,838, filed on Jan. 10, 1995, now abandoned, and a continuation-in-part of application No. 08/257,495, filed on Jun. 7, 1994, now abandoned, and a continuation-in-part of application No. 08/075,842, filed on Jun. 10, 1993, now abandoned, which is a continuation of application No. 07/678,129, filed on Apr. 1, 1991, now abandoned, said application No. 08/257,495, is a continuation of application No. 07/783,518, filed on Oct. 28, 1991, now abandoned, which is a continuation-in-part of application No. 07/678,129, which is a continuation-in-part of application No. 07/415,283, filed on Aug. 30, 1989, now abandoned.

(51) Int. Cl.[7] .............................................. C07K 5/06

(52) U.S. Cl. ..................... 514/19; 548/496; 562/573

(58) Field of Search ................. 514/19, 18; 548/496; 562/573; 530/327, 328, 329, 330, 331

(56) References Cited

U.S. PATENT DOCUMENTS

| 3,997,516 A | * 12/1976 | Nishimura ................ 260/112.5 |
| 4,191,753 A | * 3/1980 | Ryan ......................... 424/177 |
| 5,100,873 A | 3/1992 | de Castiglione et al. ...... 514/15 |
| 5,538,951 A | 7/1996 | Morozov et al. ............. 514/19 |
| 5,716,935 A | * 2/1998 | Rodgers et al. ............... 514/16 |
| 5,728,680 A | 3/1998 | Morozov et al. ............. 514/19 |
| 5,767,087 A | 6/1998 | Morozov et al. ............. 514/19 |
| 5,770,576 A | 6/1998 | Morozov et al. ............. 514/19 |

FOREIGN PATENT DOCUMENTS

| JP | 4-279597 | * 10/1992 |
| WO | WO 89/06134 | 7/1989 |
| WO | WO 92/17191 | 10/1992 |
| WO | WO 93/08815 | 5/1993 |
| WO | WO 95/03067 | 2/1995 |

OTHER PUBLICATIONS

Maione, T.E., "Direct Clinical Applications of Chemokines", IBC Conference "Chemotactic Cytokines" Oct. 26, 1995.*
Le Noble F. A. (European Journal of Pharmacology, 195 (2) 305–6, 1991.*
Deinum J. (Endocrinology 126(3) 1673–82, 1990).*
Fernandez, L. A. (Journal of laboratory and clinical medicine, 105 (2) 141–5, 1985).*
Cameron N. E. (Diabetologia 35 (1) 12_8, 1992).*
Fujita Mamoru (Biochemical and Biophysical Research Communications 294 (2) 441–7, 2002).*
Maione (Trends in Pharmacological Sciences 11, 457, 1990).*
Haber [Prog. Biochem. Pharmacol. (1976), 12 (Drugs Affecting Renin–Angiotensin–Aldosterone Syst., Proc. Kanematsu Conf. Kidney, 5th), 16–32].*
Daly, T. J. et al., "High Activity Suppression of Myeloid Progenitor Proliferation by Chimeric Mutants of Interleukin 8 and Platelet Factor 4," The Journal of Biological Chemistry, vol. 270, No. 40, Oct. 6, 1995, pp. 23282–23292.
DATABASE WPI, Section Ch, Week 9212, Derwent Publications Ltd., London, GB; Class B04, AN 92–094519, XP002023101 & SU, A, 1 642 398 (Rost Med Inst), Apr. 15, 1991. Abstract Only.
DATABASE WPI, Section Ch, Week 9501, Derwent Publications Ltd., London, GB; Class B05, AN 95–004962, XP002023100 & SU, A, 1 827 255 (Kiev Doctor Training Inst), Jul. 15, 1993. Abstract Only.
DATABASE WPI, Section Ch, Week 9511, Derwent Publications Ltd., London, GB; Class B05, AN 95–080267, XP002023102 & RU, C, 2 014 063 (Sochi Spas Physiotherapy Res. Inst), Jun. 15, 1994. Abstract only.
Folkman, J., "What Is the Evidence That Tumors Are Angiogenesis Dependent?," Journal of the National Cancer Institute, vol. 82, No. 1, Jan. 3, 1990, pp. 4–6.
Frater–Schroder et al., "Tumor necrosis factor type α, a potent inhibitor of endothelial cell growth in vitro, is angiogenic in vivo," Proc. Natl. Acad. Sci. USA, vol. 84, Aug. 1987, pp. 5277–5281.
Heimark, R.L. et al., "Inhibition of Endothelial Regeneration by Type–Beta Transforming Growth Factor from Platelets," Science, vol. 233, Sep. 5, 1986, pp. 1078–1080.
Kahn, J.O. et al., "Intralesional Recombinant Tumor Necrosis Factor–α for AIDS–Associated Kaposi's Sarcoma: A Randomized, Double–Blind Trial," Journal of Acquired Immune Deficiency Syndromes, vol. 2, No. 3, (1989) pp. 217–223.

(Continued)

Primary Examiner—Jon Weber
Assistant Examiner—David Lukton
(74) Attorney, Agent, or Firm—Burns, Doane, Swecker & Mathis, L.L.P.

(57) ABSTRACT

Disclosed are methods of inhibiting neovascularization in a subject by administering to the subject a pharmaceutical preparation of R'-Glu-Trp-R".

47 Claims, No Drawings

OTHER PUBLICATIONS

Knighton, D. et al., "Avascular And Vascular Phases Of Tumor Growth In The Chick Embryo," Br. J. Cancer, vol. 35, pp. 347–336.

Maione, T.E., "Direct Clinical Applications of Chemokines," IBC Conference "Chemotactic Cytokines" Oct. 26, 1995.

Maione, T.E. et al., "Development of angiogenesis inhibitors for clinical applications ," Trends in Pharmaceutical Sciences, vol. 11, Nov. 1990, pp. 457–460.

Nakamura, S. et al., "Kaposi's Sarcoma Cells: Long–Term Culture with Growth Factor from Retrovirus–Infected CD4+ T Cells," Science, vol. 242, Oct. 21, 1988, pp. 426–430.

Rodionov et al., "The Immunocorrective Therapy of Pyoderma Caused by Staphylococci Multiply Resistant to Antibiotics," Vestn. Dermatol. Venerol, vol. 1, (Medline Abstract No. 90224329) (1990) pp. 42–45.

Sidky, Y.A. et al., "Inhibition of Angiogenesis by Interferons: Effects on Tumor– and Lymphocyte–induced Vascular Responses," Cancer Research,. vol. 47, Oct. 1, 1987, pp. 5155–5161.

Wiseman, D.M. et al., "Transforming Growth Factor–Beta (TGFβ) Is Chemotactic For Human Monocytes And Induces Their Expression of Angiogenic Activity," Biochemical and Biophysical Research Communications, vol. 157, No. 2, Dec. 15, 1988, pp. 793–800.

* cited by examiner

PHARMACEUTICAL ANGIOSTATIC DIPEPTIDE COMPOSITIONS AND METHODS OF USE THEREOF This application is a continuation of Ser. 09/260190, filed Mar. 1, 1999, now U.S. Pat. No. 6,096,713. Application Ser. No. 09/260190 is a continuation of application Ser. No. 08/614764, filed Mar. 13, 1996, now U.S. Pat. No. 5,902,790. Application Ser. No. 08/614764 is a continuation of application Ser. No. 08/538701, filed Oct. 3, 1995, now abandoned. Application Ser. No. 08/538701 is a continuation-in-part of application Ser. No. 08/278463, filed Jul. 21, 1994, now abandoned. Application Ser. No. 08/278463 is a continuation-in-part of Ser. No. 08/401653 filed Mar. 9, 1995, now abandoned, and a continuation-in-part of Ser. No. 08/257495 filed Jun. 7, 1994, now abandoned, and a continuation-in-part of Ser. No. 08/370838 filed Jan. 10, 1995, now abandoned, and a continuation-in-part of Ser. No. 08/075842 filed Jun. 10, 1993, now abandoned. Application Ser. No. 08/075842 is a continuation of Ser. No. 07/678129 filed Apr. 1, 1991, now abandoned. Application Ser. No. 08/257495 is a continuation of Ser. No. 07/783518, filed Oct. 28, 1991, now abandoned, which is a continuation-in-part of Ser. No. 07/678129, which is a continuation-in-part of Ser. No. 07/415283, filed Aug. 30, 1989, now abandoned.

BACKGROUND OF THE INVENTION

The present invention relates generally to pharmaceutical compositions containing peptides having angiostatic properties and more particularly to pharmaceutical compositions of tryptophan-containing dipeptides and methods of use thereof.

Neovascularization, the genesis of new blood vessels, is triggered early in embryogenesis and also during wound healing, tissue remodeling and probably in the normal course of maintenance of the vascular system. Processes involved in neovascularization include at least endothelial cell and pericyte activation; basal lamina degradation; migration and proliferation of endothelial cells and pericytes; formation of a new capillary vessel lumen; appearance of pericytes around the new vessels; development of a new basal lamina; capillary loop formation; persistence of involution with differentiation of the new vessels; capillary network formation; and, eventually, of the network organization into larger microvessels.

Certain cytokines are known to down-regulate neovascularization, including interleukin-12 (IL-12), transforming growth factor-β (TGF-β), interferon-α (IFN-α) and platelet factor 4 (PF-4). However, clinical experience with cytokine therapy has proven problematic due to the toxicity of certain of these compounds.

There are a number of pathologic conditions in which angiogenesis either plays a role in or is involved directly in different sequelae of the disease. These include, for example, neovascularization of tumors in cancer; creation of hemangeomas; neovascularization associated with various liver diseases; angiogenic dysfunction related to an excess of hormone; neovascular sequelae of diabetes; neovascular sequelae to hypertension; neovascularization in post-recovery cerebrovascular accident; neovascularization due to head trauma; neovascularization in chronic liver infection; restenosis following angioplasty; and neovascularization due to heat or cold trauma.

While angiogenesis is undoubtedly required for maintenance of a healthy vascular system, clinical medicine would appreciate the availability of a non-toxic treatment for temporarily down-regulating neovascularization, i.e., inducing a temporary angiostasis.

SUMMARY OF THE INVENTION

L-Glu-L-Trp has been known to stimulate the production of immune cells and to normalize their numerical relationship in immune deficiency conditions. (See, e.g., WO 89/06134, WO 92/17191 and WO 93/08815.) However, it has been discovered here that the dipeptide also has angiostatic activity independent of its effect in immune deficiency conditions. The results of studies in vitro showed that low levels of L-Glu-L-Trp dipeptide inhibit neovascularization of chicken chorioallantoic membranes during embryogenesis. In animal studies, L-Glu-L-Trp inhibited neovascularization of Lewis lung tumor when injected intradermally in C57BL/6 mice, and inhibited growth of Sarcoma 180 in Swiss-Webster mice.

Accordingly, this invention provides methods of treating a subject having a pathologic condition involving neovascularization by administering a phamiaceutical preparation comprising an R'-Glu-Trp-R' dipeptide and a pharmaceutically acceptable carrier to the subject in an amount effective to inhibit neovascularization.

In particular, this invention provides methods of treating subjects having the following pathologic conditions involving neovascularization: hemangiomas; vascularized malignant and benign tumors, including as tumors of the meninges, intracerebral tumors, sarcomas, osteosarcomas, soft tissue tumors such as those of the esophagus and trachea; substance-induced neovascularization of the liver, including that induced secondary to ingestion of drug, alcohol or substances of abuse; angiogenic dysfunction related to an excess of hormone, e.g., estrogen; neovascular sequelae of diabetes, such as central serous chorioretinopathy; neovascular sequelae to hypertension;

neovascularization in post-recovery cerebrovascular accident; neovascularization due to head trauma; chronic liver infection (e.g., chronic hepatitis); restenosis following angioplasty; and neovascularization due to heat or cold trauma, such as burn or frostbite. The dipeptide exhibits this activity both in subjects with healthy immune systems, i.e., who are not immune compromised, as well as those subjects who are immune compromised.

DETAILED DESCRIPTION OF THE INVENTION

The present invention provides pharmaceutical Glu-Trp preparations comprising an R'-Glu-Trp-R" dipeptide and a pharmaceutically acceptable carrier. R'-Glu-Trp-R" dipeptide, as used herein, refers to the dipeptide L-Glu-L-Trp and derivatives or analogues thereof.

As used herein, a derivative of the R'-Glu-Trp-R" dipeptide includes those in which the dipeptide is derivatized by the covalent attachment of a moiety at R' and/or R". This includes, for example, pharmaceutically acceptable salts of the dipeptide, amides, imides, esters, anhydrides, ethers, methyl or ethyl-alkyl esters, alkyl, aryl or mixed alkyl/aryl derivatives where the formula weight is less than about 5000 Daltons or less than 1000 Daltons, multimeric or cyclic versions of the dipeptide and peptides of fewer than about 20 amino acids or less than about 10 amino acids that include glu-trp within their amino acid sequence. Representative examples include HEW, EWEW, (SEQ ID NO 1), GEW, EWKHG (SEQ ID NO 2), EWKKHG (SEQ ID NO 3), EW-NH-NH-GHK-NH2, Ac-L-Glu-L-Trp-OH, Suc-EW, Cpr-EW, But-EW, RKEWY (SEQ ID NO 4), RKEW (SEQ ID NO 5), KEWY (SEQ ID NO 6), KEW, pEW.

As used herein, analogs of R'-Glu-Trp-R" dipeptide include those in which L-amino acids are substituted for D-amino acids, such as L-Glu-D-Trp, D-Glu-L-Trp or D-Glu-D-Trp, and analogs of tryptophan such as 5-hydroxy-tryptamine, 5-hydroxy-indol-acetic acid and pyrole analogs in which the nitrogen in the pyrole ring is replaced with carbon.

L-Glu-Trp-L presently is the most preferred R'-Glu-Trp-R" dipeptide. L-Glu-L-Trp is also referred to herein interchangeably as "EW" and "EW dipeptide", using the single letter convention wherein the first named amino acid is the amino terminus and the last named amino acid is the carboxyl terminus.

As used herein, "neovascularization" refers to the generation of new blood vessels. The process by which new blood vessels are formed may involve processes of endothelial cell and pericyte activation; basal lamina degradation; migration and proliferation (i.e., cell division) of endothelial cells and pericytes; formation of a new capillary vessel lumen; appearance of pericytes around the new vessels; development of a new basal lamina; capillary loop formation; persistence of involution, and differentiation of the new vessels; and, capillary network formation and, eventually, organization into larger microvessels. As referred to herein the process of endothelial cell proliferation, e.g., in a vascular bud, is termed "angiogenesis" and is related to neovascularization as a subprocess. Representative clinical diagnostic manifestations of diseases have been classified and codified (International Classification of Diseases, ICD-9-CM, Washington, D.C. 1989.) Representative laboratory indicia of neovascularization include (but are not limited to) data e.g. collected in angiograms, CAT scans and sonograms, as well as visual examination by endoscopic and/or capillaroscopic procedures.

As used herein the terms "angiostasis," "angiostatic" and "inhibition of neovascularization" mean that the rate or extent of neovascularization in a tissue is decreased from a pre-treatment value to a post-treatment value. Angiostasis may be determined using laboratory or clinical indicia of disease activity, above. Angiostasis may involve inhibiting one or more subprocesses involved in neovascularization, e.g., endothelial or vascular smooth muscle cell proliferation or migration.

As used herein, a "pathologic condition involving neovascularization" refers to a pathologic condition in which neovascularization or the risk of it is a component. This includes, without limitation, pathologies in which neovascularization is the primary pathology, such as hemangiomas; pathologies in which neovascularization is not the primary pathology but contributes to it, such as neovascularization of tumors; and pathologies in which neovascularization is a sequela of the primary disease, such as central serous retinopathy in diabetes.

As used herein, the term "subject" refers to a mammal, including human and non-human primates, domestic animals and livestock, fur bearing animals, and the like, e.g., dogs, cats, rodents, birds, horses, cows, pigs, fish, and the like. Embodiments of the invention encompass therapeutic and prophylactic treatment methods for use in subjects in need thereof.

As used herein the term "immune compromised" refers to a person having a lower than normal number of one or more immune cells, such as NK cells, T4 or T8 T-lymphocytes, B-lymphocytes, or phagocytes, as measured by standard clinical diagnostic indicia. It also includes individuals having diminished function of immune cells as determined by standard functionality testing of such cells, e.g., production of immunoglubulins, chemotaxis, mixed leukocyte reaction or delayed hypersensitivity assay. Immune compromised individuals often present with unusual or unexpected opportunistic infections.

"Polypeptide" is intended to mean a serial array of amino acids of more than 16 and up to many hundreds of amino acids in length, e.g., a protein.

"Abnormal" as used herein refers to laboratory indicia of neovascularization that are outside of the range of values recorded in healthy individuals.

"Normalized" as used herein refers to changes in laboratory or clinical indicia of neovascularization that are, following treatment, returned to within the normal range of values recorded for normal healthy subjects. A subject without a vascular defect and without a known deficiency in any coagulation, fibrinolytic, or vascular system is referred to herein interchangeably as "a normal subject".

As used herein, the terms "modulator" and "modulating" mean the agent and process of decreasing neovascularization or angiogenesis in a normal subject or in a compromised subject.

R'-Glu-Trp-R" treatment is intended to mean a method of delivering to a subject in need thereof a pharmaceutical preparation of R'-Glu-Trp-R" with the aim of inducing a decrease in the rate or extent of neovascularization or angiogenesis.

In one presently preferred embodiment, an R'-Glu-Trp-R" pharmaceutical preparation is administered to a cancer patient in an amount and for a time sufficient to decrease one or more clinical or laboratory indicia of neovascularization or angiogenesis, thereby effecting improvement in the clinical condition of the patient so treated. This method decreases neovascularization in the tumor, inhibiting blood supply to the tumor and, thereby, inhibiting growth of the tumor.

In a preferred embodiment a treatment regimen consists of administering a dose of about 0.5 μg per 1 kilogram body weight to about 1 mg per 1 kg body weight daily over a period of 1 day to about 30 days to the subject. In preferred embodiments the subject dose is administered either as a single daily intramuscular dose of the R'-Glu-Trp-R" pharmaceutical preparation (intramuscularly), or as a single daily intranasal dose of the R'-Glu-Trp-R" pharmaceutical preparation (intranasally). The subject dose is preferably formulated as a sterile, injectable, inhalant, nose drop, or mucosal spray solution containing about 0.001% to about 0.01% of the R'-Glu-Trp-R" pharmaceutical preparation. Alternatively, the formulation of the R'-Glu-Trp-R" pharmaceutical preparation may preferably be incorporated into a unit dose delivery form e.g., a tablet, a suppository, a capsule, an eye film, or into a paste or ointment, e.g., a toothpaste, a dermal ointment, or water-soluble cream base. A most preferred unit dose form is for delivery of about 0.01 mg of the R'-Glu-Trp-R" pharmaceutical preparation.

The subject methods of the invention find a variety of prophylactic and therapeutic uses in treatment of pathophysiologic conditions in humans and domestic animals. In certain embodiments the methods of the invention find use during in vitro maintenance of endothelial cell cultures and vascular tissues such as may occur prior to autologous or allogenic grafting. The methods involve maintaining endothelial cell cultures or vascular tissue cultures in vitro by culturing the tissues in a culture medium comprising an R'-Glu-Trp-R" compound. The subject maintenance method has the advantage of maintaining vascular tissues and reducing inflammatory alterations triggered by the tissue trauma occurring during surgical removal and storage in tissue culture.

In a representative prophylactic treatment regimen, the subject compositions of the invention are administered to a patient susceptible to or otherwise at risk for developing neovascularization, e.g., in post-surgical use to prevent neovascularization of a recurring primary tumor or it metastatic cells. "Prophylactically effective dose" is used herein to mean an amount sufficient to produce an angiostatic effect at a tissue site, wherein the amount will depend on the patient's state of health and weight, but will generally fall within the ranges described herein for therapeutic use. Prophylactic administration may be particularly desirable for subjects that are at risk of disease sequelae involving neovascularization or angiogenesis as a complication, e.g., diabetic retinopathy.

Embodiments of the invention include therapeutic treatment regimens wherein an R'-Glu-Trp-R" pharmaceutical preparation is administered alone, or in combination with a second pharmaceutical agent, i.e., "combined therapy".

Representative combined therapies include those in which an R'-Glu-Trp-R" composition is administered with one or more antibiotics, anti-inflammatory agent, or chemotherapeutic compounds. The subject compositions may be administered either in conjunction with the second treatment modalities, or separately, e.g. at different times or in different syringes or tablets. Often, R'-Glu-Trp-R" is administered in a combined therapy with anti-inflammatory agents, antihistamines, chemotherapeutic agents and the like. Illustrative combined treatments with R'-Glu-Trp-R" may include, e.g., anti-inflammatory agents well known in the art.

Illustrative combined treatments with R'-Glu-Trp-R" may also include administration of a vasoactive drug as the second agent. Representative vasoactive drugs so active include drugs in the class of angiotensin converting enzyme (ACE) inhibitors, potassium channel openers (PCO) and the like.

Illustrative combined cancer treatments with R'-Glu-Trp-R" include administration of a chemotherapeutic agent as the second agent. Treatments with R'-Glu-Trp-R" may be effective to decrease undesirable side-effects associated with a corticosteroid therapy, e.g., neovascularization. Representative chemotherapeutic agents are well known in the art.

Skilled practitioners will adjust the timing and dosage to fit the clinical symptoms of the patients. Such knowledge has been accumulated over decades, and is reported in the medical literature as well as medical texts. The timing of when to start the subject methods in combination or single agent therapy rests on the physician's clinical judgment.

Empirical therapy is a therapy designed to treat the most common or likely causative agent based on historic, demographic, and epidemiologic information. Empirical therapy may often include use of multiple therapeutic agents designed to cover a wide range of therapeutic possibilities. When laboratory test data are available the choice of therapy may be adjusted to more particularly treat the disease. Because treatment of clinical syndromes is very often initiated empirically. Rather, a new therapeutic method must be tested for a particular clinical syndrome.

In the art of pharmaceutical drug development, preclinical studies of a therapy evaluate the therapy's effects on not just one condition, but on multiple agents or conditions of interest. The results of the various (sometimes equivocal) studies are weighed as to the benefits and risks of the particular therapy given the medical knowledge of the risks associated with a particular disease.

It is common that not all patients with a syndrome are cured by a single therapy, but instead, that a subset of patients may exist wherein the therapy has a positive and favorable result. Examples of clinical syndromes in which subsets of patients may find favorable outcomes from the subject therapies of the invention are disclosed in the following several paragraphs.

The pharmaceutical compositions of the invention are intended for parenteral, topical, subcutaneous, intramuscular, intrathecal, oral, intranasal, intraperitoneal or local administration (e.g. on the skin in a cream), or prophylactic and/or therapeutic treatment. Preferably, the compositions of the present invention are administered parenterally, intramuscularly or intranasally. The subject R'-Glu-Trp-R" compositions herein have the advantage of providing the desired effects at very low dosage levels and without toxicity. Thus, a purpose of therapy in an acute setting may be to rapidly increase the concentration of R'-Glu-Trp-R" in a tissue, e.g., by bolus intravenous injection or infusion. Alternatively, in other cases it may desirable to deliver R'-Glu-Trp-R" over a longer period of time.

The subject compositions containing R'-Glu-Trp-R" may be formulated in a manner that allows absorption into the blood stream. The present compositions are vascular modulators that induce changes at the cellular level that subsequently effect changes in cellular processes that no longer are dependent on the presence of the composition. It has been observed that the effects of the peptide may be long lasting, i.e., for weeks to months, despite the rather rapid degradation of the peptide, e.g. within 5 minutes. Although the subject R'-Glu-Trp-R" compounds are themselves water-soluble at the low concentrations in which they are usually employed, they are preferably used in the form of their acid or alkaline salts formed with pharmaceutically acceptable agents, e.g., acetic, citric, maleic, succinic acid, sodium, potassium, ammonium, or zinc. Freely-soluble salts of the subject R'-Glu-Trp-R" compositions may also be converted to salts of low solubility in body fluids e.g., by modification with a slightly water-soluble pharmaceutically acceptable salt like tannic or palmoic acid, or by inclusion in a time-release formulation with covalently coupling to a larger carrier, or inclusion in timed-release capsule and the like.

The subject R'-Glu-Trp-R" pharmaceutical preparations may be used as free peptides or in the form of a water soluble pharmaceutically acceptable salts, such as a sodium, potassium, ammonium or zinc salt. It will be understood that the subject dipeptides may be administered with other active ingredients which independently impart an activity to the composition. Pharmaceutically acceptable salts may be conveniently prepared from an R'-Glu-Trp-R" dipeptide (or its agonist) by conventional methods. Thus, such salts may be, for example, prepared by treating R'-Glu-Trp-R" dipeptide with an aqueous solution of the desired pharmaceutically acceptable metallic hydroxide or other metallic base and evaporating the resulting solution to dryness, preferably under reduced pressure in a nitrogen atmosphere. Alternatively, a solution of R'-Glu-Trp-R" dipeptide may be mixed with an alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosulate, citrate, maleate, fumate, succinate, tartrate, and the like.

For parenteral administration the present invention provides pharmaceutical preparations for parenteral administration which comprise a solution of R'-Glu-Trp-R" dipeptide, or polymeric, multimeric, or cyclic forms or derivative thereof, dissolved in a pharmaceutically acceptable carrier, preferably an aqueous carrier. A variety of aqueous carriers may be used, e.g., water, buffered water, 0.4% saline, 0.3% glycine, and the like, including proteins and/or glycoproteins for enhanced stability, such as albumin, lipoprotein, globulin, and the like. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administrations. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. It may be desirable to stabilize R'-Glu-Trp-R" dipeptides, analogs, derivatives, agonists, and the like to increase their shelf life and pharmacokinetic half-life. Shelf life stability is improved by adding excipients such as: a) hydrophobic agents (e.g., glycerol); b) sugars (e.g., sucrose, mannose, sorbitol, rhamnose, xylose); c) complex carbohydrates (e.g., lactose); and/or d) bacteriostatic agents. Pharmacokinetic half-life of peptides is modified by coupling to carrier peptides, polypeptides, and carbohydrates by chemical derivatization (e.g., by coupling side chain or N- or C-terminal residues), or chemically altering the amino acid to another amino acid (as above). Pharmacokinetic half-life and pharmacodynamics may also be modified by: a) encapsulation (e.g., in liposomes); b) controlling the degree of hydration (e.g.,. by controlling the extent and type of glycosylation of the peptide); and, c) controlling the electrostatic charge and hydrophobicity of the peptide.

The R'-Glu-Trp-R" dipeptide containing compositions according to the present invention may be administered in a compatible pharmaceutical suitable for parenteral administration (e.g., intravenous, subcutaneous, intramuscular). The preparations may be subjected to conventional pharmaceutical operations, such as sterilization, and may contain adjuvants, such as preservatives, stabilizers, wetting agents and the like.

The R'-Glu-Trp-R" dipeptide compositions are typically biologically active at a dose of about 0.5 $\mu$g/kg to about 1 mg/kg, preferably about 1 $\mu$g/kg to about 50 $\mu$g/kg. The concentration of the R'-Glu-Trp-R" dipeptides in pharmaceutical compositions can vary, i.e., from about 0.001% to as much as 15 or 20% by weight and will be selected primarily by fluid volumes, viscosities, etc., in accordance with the particular needs of the treatment and mode of administration to a patient. When utilized intramuscularly as an injection solution with the active ingredient in a amount effective to inhibit neovascularization, e.g., about 0.001 to 0.01% by weight of R'-Glu-Trp-R". If prepared in the form of a tablet, capsule or suppository, it is preferred that the active ingredient be present in an amount of about 0.1 mg of R'-Glu-Trp-R" per tablet, suppository or capsule. The pharmaceutically acceptable vehicle for this injection form may be any pharmaceutically acceptable solvent such as 0.9% aqueous sodium chloride, distilled water, Novocaine solution, Ringer's solution, glucose solution, and the like. In such form, the capsule, suppository or tablet may also contain other conventional excipients and vehicles such as fillers, starch, glucose, etc. In topical preparations, the R'-Glu-Trp-R" dipeptides are generally contained in urea-based emollients, petroleum-based ointments, and the like at concentrations of about 0.1 to 10,000 parts per million, preferably about 1 to 1000 parts per million, and most preferably about 10 to 100 parts per million. Actual methods for preparing parenterally, orally, and topically administrable compounds will be known or apparent to those skilled in the art and are described in detail in, for example, Remington's Pharmaceutical Science, 17th ed., Mack Publishing Company, Easton, Pa. (1985), which is incorporated herein by reference.

Intramuscular and intranasal routes are preferred for administration of the subject R'-Glu-Trp-R" compositions. One preferred dosage of the subject composition for intramuscular administration is about 50 $\mu$g to 100 $\mu$g R'-Glu-Trp-R" per dose for adults (for a 300 $\mu$g to 1000 $\mu$g total treatment therapy); for infants up to 1 year old about 10 $\mu$g per dose, for infants 1 to 3 years old about 10 $\mu$g to 20 $\mu$g per dose; for infants 4 to 6 years old about 20 $\mu$g to 30 $\mu$g per dose, for children 7 to 14 years old about 50 $\mu$g per dose. All of the foregoing dosages are useful for a treatment of 3 to 10 days, depending upon the needs of the patient. The treatment may be repeated as needed, usually within 1 to 6 months. In another preferred embodiment a treatment dose of about 10 $\mu$g/kg to about 1 mg/kg of a R'-Glu-Trp-R" pharmaceutical preparation administered to a subject daily over a period of about 6 days to about 10 days but optionally at the discretion of the attending physician for up to about 30 days. In one preferred course of therapy R'-Glu-Trp-R" is administered im daily at a dosage of 1–100 $\mu$g/kg for 5–7 days, followed by a 1–6 month intermission before repeating the same injection regimen.

The R'-Glu-Trp-R" composition may be administered alone or formulated with pharmaceutically acceptable carriers, in either single or multiple doses. Suitable pharmaceutical carriers include inert solid diluents or fillers, sterile aqueous solutions, and various nontoxic organic solvents. The pharmaceutical compositions formed by combining R'-Glu-Trp-R" dipeptide with a pharmaceutically acceptable carrier and an optional antibiotic. The subject combination therapeutic agents are then readily administered in a variety of dosage forms such as tablets, lozenges, syrups, injectable solutions, and the like. Combination therapeutic agents may also include R'-Glu-Trp-R" dipeptide, e.g., L-Glu-L-Trp, in the same unit dosage form. Pharmaceutical carriers can, if desired, contain additional ingredients such as flavorings, binders, excipients, and the like.

Thus, for purposes of oral administration, tablets containing various excipients such as sodium citrate, calcium carbonate, and calcium phosphate may be employed along with various disintegrants such as starch, and preferably potato or tapioca starch, alginic acid, and certain complex silicates, together with binding agents such as polyvinylpyrrolidone, sucrose, gelatin, and acacia. Additionally, lubricating agents, such as magnesium stearate, sodium lauryl sulfate, and talc are often useful for tableting purposes. Solid compositions of a similar type may also be employed as fillers in salt and hard-filled gelatin capsules. Preferred materials for this purpose include lactose or milk sugar and high molecular weight polyethylene glycols. When aqueous suspensions of elixirs are desired for oral administration, the essential active R'-Glu-Trp-R" dipeptide ingredients therein may be combined with various sweetening or flavoring agents, colored matter or dyes, and if desired, emulsifying or suspending agents, together with diluents such as water, ethanol, propylene glycol, glycern, and combinations thereof.

For parenteral administration, solutions of R'-Glu-Trp-R" in sesame or peanut oil or in aqueous polypropylene glycol may be employed, as well as sterile aqueous saline solutions of the corresponding water soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous, and intraperitoneal injection. The sterile aqueous media employed are all readily obtainable by standard techniques well known to those skilled in the art. Additionally, it is possible to administer the aforesaid compounds topically (e.g., through a placed catheter) using an appropriate solution suitable for the purpose at hand.

An amount adequate to effect a therapeutic result in more than 50% of subjects so treated is defined as a "therapeutically effective dose." Treatment of acute conditions generally will occur over about 3–10 days. Treatment of chronic conditions or prophylactic treatments have the same course, but can be repeated after as long as about 1–6 months or longer. In some instances, it may be desirable to administer the compositions intermittently on a daily basis for periods of about 2 to about 20 days, preferably about 3 to about 14 days, more preferably about 4 to about 10 days which are repeated at least about 15 days, preferably about 20 days or as much as about 1 to 6 months or more.

The route of delivery of a R'-Glu-Trp-R" composition is determined by the disease and the site where treatment is required. For topical application it may be desirable to apply the R'-Glu-Trp-R" composition at the local site (e.g., by placing a needle into the tissue at that site) or by placing an impregnated bandage e.g. at a tumor site following surgical removal; while for other diseases it may be desirable to administer the R'-Glu-Trp-R" compositions systemically. For other indications the R'-Glu-Ttp-R" compositions and the like may be delivered by intravenous, intraperitoneal, intramuscular, subcutaneous, intranasal, and intradermal injection, as well as, by intrabronchial instillation (e.g., with a nebulizer), transdermal delivery (e.g., with a lipid-soluble carrier in a skin patch), or gastrointestinal delivery (e.g., with a capsule or tablet).

In general, the acid addition salts of the subject R'-Glu-Trp-R" composition, e.g., L-Glu-L-Lys, compositions with pharmaceutically acceptable acids will be biologically equivalent to the subject R'-Glu-Trp-R" composition themselves.

The preferred therapeutic compositions, inocula, routes, and dosage will of course vary with the clinical indication. For intramuscular injection the inocula is typically prepared from a dried peptide (or peptide conjugate) by suspending the peptide in a physiologically acceptable diluent such as water, saline, or phosphate-buffered saline. Some variation in dosage will necessarily occur depending upon the condition of the patient being treated, and the physician will, in any event, determine the appropriate dose for the individual patient. The effective amount of peptide per unit dose depends, among other things, on the body weight, physiology, and chosen inoculation regimen. A unit does of peptide refers to the weight of peptide without the weight of carrier (when carrier is used). An effective treatment will be achieved when the concentration of R'-Glu-Trp-R" dipeptide, e.g., L-Glu-L-Trp, at a tissue site in the microenviroment of the cells approaches a concentration of $10^{-5}$ M to $10^{-9}$ M. Skilled practitioners can make use of clinical and laboratory indicia (above) to monitor patient response to the subject therapy and adjust the dosage accordingly. Since the pharmacokinetics and pharrnacodynamics of R'-Glu-Trp-R" dipeptides, agonists, antagonists, and the like will vary in different patients, a most preferred method for achieving a therapeutic concentration in a tissue is to gradually escalate the dosage and monitor the clinical and laboratory indicia (above). The initial dose, for such an escalating dosage regimen of therapy, will depend upon the route of administration. For intravenous administration, of R'-Glu-Trp-R" dipeptide with an approximate molecular weight of 200 to 400 daltons, an initial dosage of approximately 0.5 µg/kg body weight is administered and the dosage is escalated at 10-fold increases in concentration for each interval of the escalating dosage regimen.

If presented in the form of a tablet, capsule or suppository it is preferred that the active ingredient be present in an amount of about 0.1 mg per tablet, suppository or capsule. If presented in such form, the capsule, suppository or tablet may also contain other conventional excipients and vehicles such as fillers, starch, glucose, etc.

Conveniently, the subject R'-Glu-Trp-R" dipeptide is synthesized by any of a number of automated techniques that are now commonly available. Generally speaking, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one amino acid and the carboxyl group of the other. The blocking groups should be selected for easy removal without adversely affecting the peptides, i.e., by racemization or by hydrolysis of the formed peptide bonds. Amino acids with carboxyl- groups (e.g., Asp, Glu) or hydroxyl-groups (e.g., Ser, homoserine, and tyrosine) also require blocking prior to condensation.

A wide variety of procedures exist for synthesis of peptides, solid-phase synthesis usually being preferred. In this procedure an amino acid is bound to a resin particle, and the peptide generated in a stepwise manner by successive additions of protected amino acids to the growing chain. Modifications of the technique described by Merrifield are commonly used. In an exemplary automated solid-phase method, peptides are synthesized by loading the carboxy-terminal amino acid onto an organic linker (e.g., PAM, 4-oxymethyl phenylacetamidomethyl) covalently attached to an insoluble polystyrene resin that is cross-linked with divinyl benzene. Blocking with t-Boc is used to protect the terminal amine, and hydroxyl- and carboxyl- groups are commonly blocked with O-benzyl groups. Synthesis is accomplished in an automated peptide synthesizer (Applied Biosystems, Foster City, Calif., e.g., Model 430-A). Following synthesis the product may be removed from the resin and blocking groups removed using hydrofluoric acid or trifluoromethyl sulfonic acid according to established methods (Bergot, B. J. and S. N. McCurdy, Applied Biosystems Bulletin, 1987). A routine synthesis can produce 0.5 mmole of peptide-resin. Yield following cleavage and purification is approximately 60 to 70%. For example, an amino and side chain protected derivative of an activated ester of Glx is reacted with side-group protected Trp, attached to the solid phase at its C-terminus. After elimination of the alpha-amino protecting group, the peptide maybe cleaved from the solid phase or another amino acid added in a similar fashion.

Additional amino acids are serially added. The peptides are cleaved by highly acidic cleavage that also typically removes protecting groups.

The peptides may then be isolated and lyophilized and stored for future use. Suitable techniques of peptide synthesis are described in detail in Stewart and Young, *Solid Phase Pepride Synthesis*, 2d edition, Pierce Chemical Company, 1984; and Tam et al., J. Am. Chem. Soc., 105:6442 (1983), both of which are incorporated herein by reference.

Purification of the product peptides is accomplished for example by crystallizing the peptide from an organic solvent such as methyl-butyl ether, followed by dissolving in distilled water, and dialysis (if greater than about 500 molecular weight), thin layer chromatography, gel chromatography, lyophilization, or reverse HPLC (e.g., using a C18 column with 0.1% trifluoroacetic acid and acetonitrile as solvents) if less than 500 molecular weight. Purified peptide is lyophilized is stored in a dry state until use. A representative R'-Glu-Trp-R" pharmaceutical preparation is the purified dipeptide L-Glu-L-Trp, which comprises a white powder (if lyophilized; otherwise, it is crystalline), soluble in water, DMF; insoluble in chloroform and ether. [alpha$22_D$=+12.6; C=0.5 $H_2O$. $R_f$=0.65 (butanol: acetic acid: water=3:1:1). UV (275±5 nm, max). NMR (500 MHz): 0.001 mol/1 of the peptide solution, Trp (3.17; 3.37; 4.57; 7.16; 7.24; 7.71; 7.49); Glu (1.90; 1.96; 2.21; 3.72).

Typically an amino and side chain protected derivative of an activated ester of glutamic acid is reacted with protected L-tryptophan. After elimination of the protecting groups and conventional purification, such as by thin layer or GL chromatography, the peptide may be purified such as by, lyophilization, gel purification, and the like.

While not wishing to be tied to any particular mechanism of action, it is believed possible that the subject tryptophan-containing peptides may reversibly associate with specific cellular EW receptors on endothelial cells, one such receptor being defined as the ubiquitous "CD2" cell surface determinant present also on lymphocytes, endothelial cells and certain epithelial cells. It is thought possible that binding of EW dipeptide to CD2 (and other EW receptors) triggers a conformational change in the receptor that may initiate up-regulation of adenylate cyclase and increased intracellular cAMP. It is presently believe possible that L-Glu-L-Trp exerts its effects by down-regulating cellular mechanisms by which inflammatory mediators such as TNF-α and IL-1 trigger endothelial cell and pericyte activation and proliferation. Activation results in changes in cell surface expression of adhesins involved in binding inflammatory cells in vasculitis, while proliferation is involved in neovascularization. L-Glu-L-Trp down-regulation of inflammatory mediator-induced endothelial effects may involve dephosphorylation of one or more cellular tyrosine kinases. It is considered likely that such down-regulation may result in changes in synthesis or cell surface expression of endothelial adhesins, selecting, and/or integrins. e.g., ELAM, VCAM, and the like. The latter cellular changes induced by tryptophane-containing dipeptides may result in a decreased ability of inflammatory cells (e.g., lymphocytes, neutrophils, and/or monocytes) to localize at sites of vasculitis.

As used herein the symbols for amino acids are according to the IUPAC-IUB recommendations published in Arch. Biochem. Biophys. 115: 1–12, 1966 with the following single letter symbols for the amino acids: L, Leu, Leucine; V, Val, Valine; Y, Tyr, Tyrosine; D, Asp, Aspartic Acid; W, Trp, Tryptophan; P, Pro, Proline; I, Ileu, Isoleucine; G, Gly, Glycine; M, Met, Methionine; E, Glu, Glutamic Acid; T, Thr, Threonine; K, Lys, Lysine; N, Asn, Asparagine; R, Arg, Arginine; Q, Gln, Glutamine; A, Ala, Alanine; C, Cys, Cysteine; S, Ser, Serine; F, Phe, Phenylalanine; H, His, Histidine; C, Cys, Cysteine; S, Ser, Serine.

The following examples are provided to further elucidate the invention, but are not intended to restrict the invention in scope or spirit in any way.

EXAMPLE 1

Lack of Mutagenicity and Toxicity of L-Glu-L-Trp: Pharmacokinetics and Biodistribution

*Note that general materials and methods used in Examples, below, appear at the end of the Examples section and immediately before the citations.

Protocol A

Acute Toxicity Studies

Summary: L-Glu-L-Trp when injected im at dosages calculated to be about 10,000-times a therapeutic dosage were non toxic in mice, guinea pigs, chickens, and dogs as determined by monitoring general condition, behavior, movements, cardiac and respiratory physiology, and gross pathology.

Protocol B

Chronic Toxicity Studies

Summary: L-Glu-L-Trp when injected daily as a single im or iv for a period of 28 days was without adverse effects as determined by monitoring behavior, feeding, body weight, coat condition, mucous membranes, red and white cell blood counts, cardiac and respiratory physiology, liver and kidney function, and gross pathology. Kidney function was determined by evaluation of diuresis after water-loading; for certain other experiments dogs and rats were sacrificed and examined after 10, 20, 30, and 60 days.

Protocol C

Pharmacokinetics and Biodistribution: GLP Study $^{14}$C-radiolabeled L-Glu-L-Trp (110 µg/kg) was administered intranasally to Sprague-Dawley rats. Blood and tissue samples were collected at different 0.5, 2, 8 or 24 hours and the amount of intact L-Glu-L-Trp was determined by HPLC. Tissue samples included packed red blood cells, white blood cells, liver, kidney, heart, lung spleen, thymus, brain, muscle, skin, fat, eye, ovaries, testes, submandibular lymph nodes, and the gastrointestinal tract with contents. Intranasally administered $^{14}$C-L-Glu-L-Trp was rapidly absorbed with a plasma $C_{max}$ of 0.349 µg*eq.*hr/g of the $^{24}$C. No intact compound was detected in blood at 30 minutes to a sensitivity in the range of 5–101 ng/mL, suggesting a blood half life of less than 30 minutes. Tissue elimiration half-life was determined to be 18.7 hr.

EXAMPLE 2

Inhibitory Effects of L-Glu-L-Trp on Angiogenesis in Chorioallantoic Membrane (CAM) Assays Briefly, eight-day chicken embryos were removed from eggs and placed into sterile petri dishes. Individual filter paper disks were saturated with 7.5 μl of different stock solutions of L-Glu-L-Trp dissolved in sterile 0.14M NaCl to achieve final test concentrations of 0.001, 0.01, 0.1, 1.0, 10, 100, 500, and 1000 μg per disk. Disks were air dried and then inverted onto the surface of the respective embryos. Embryo vascularization was assessed after 48 hrs. of incubation using the grading scale summarized in TABLE 1, below.

TABLE 1

Scoring of Chicken Embryo Vascularity: CAM Assay

| Inhibition Grade | Description | Percentage Inhibition |
|---|---|---|
| 0 | Not visibly difference than negative control | 0 |
| 1 | Slight inhibition of vessel formation | 25 |
| 2 | Moderate inhibition of vessel formation | 50 |
| 3 | Near-complete inhibition of vessel formation | 75 |
| 4 | Complete inhibition of vessel formation | 100 |

In this experiment saline served as a negative control and 10 μg/disk of heparin served as a positive control. The pentapeptide Thr-Ala-Glu-Glu-Lys (TAEEK) (SEQ ID NO 7) served as a specificity control, (i.e., for possible nonspecific effects of peptides on neovascularization at the concentrations tested). Nine-12 test disks and a corresponding number of different embryos were employed for each test concentration along with 82 (each) positive and negative control embryos. The results are summarized in the following TABLE.

The results show a 30–88% decrease in vascularity in embryos treated with 10 ng–1000 μg of L-Glu-L-Trp in saline. The level of inhibition achieved at the 10–1000 μg doses approximated that with heparin (10 μg). Although some presumed nonspecific effects of control pentapeptide TAEEK on embryo vascularity was observed at the higher doses (i.e., 100–1000 μg), the effect was not as pronounced as that achieved with L-Glu-L-Trp and the presumptive nonspecific effect was not observed at lower doses. Taken together these results suggest an effect of L-Glu-L-Trp on the process of vessel formation in embryonic chicken tissues.

EXAMPLE 3

Inhibition of Neovasculanzation of Lewis Carcinoma

Lewis lung carcinoma cells ($5 \times 10^7$) when injected (0.1 ml) intradermally into both flanks of C57BL/6 mice (day 0) produce a visible highly vascularized tumor nodules within 7 days. By excising the tumor the degree of tumor vascularity may be determined microscopically by counting the number of large vessels radiating from the tumor mass. An independent study was performed (as follows) at a GLP approved contract research organization.

Saline was used as a negative control and Cytoxan as a positive control. The positive control, Cytoxan (200 mg/kg), was administered only on day 2. Test treatments with L-Glu-L-Trp were administered im on a daily basis starting on day 1 after tumor injection and continuing for 5 days (i.e., through day 6). L-Glu-L-Trp was administered at doses of 125, 250, 500, 1000, and 2000 μg/kg/dose. The negative control, saline, was administered ip on the same daily 5 day schedule. Ten mice (20 tumors) were evaluated at each dose of test or control agent. The results are summarized in the following TABLE.

TABLE 2

Results of Chicken Embryo CAM Assay

| Test Article | No. Embryo | Concentration (μg/disk) | Inhibition of Neovascularization | | |
|---|---|---|---|---|---|
| | | | Grade/Range | Grade/Mean ± SD* | Mean % Inhibition |
| Saline | 82 | 0 | 0–0 | 0 ± 0 | 0 ± 0 |
| Heparin | 82 | 10 | 1–4 | 3.26 ± 0.73 | 81 ± 18 |
| L-Glu-L-Trp | 10 | 1000 | 2–4 | 3.3 ± 0.82 | 83 ± 20 |
| | 10 | 500 | 1–4 | 2.4 ± 0.84 | 60 ± 20 |
| | 9 | 100 | 3–4 | 3.44 ± 0.73 | 85 ± 18 |
| | 11 | 10 | 1–4 | 3.09 ± 1.14 | 78 ± 28 |
| | 12 | 1 | 1–4 | 2.33 ± 0.89 | 58 ± 23 |
| | 10 | 0.1 | 0–3 | 1.9 ± 0.88 | 48 ± 23 |
| | 10 | 0.01 | 1–2 | 1.5 ± 0.53 | 38 ± 13 |
| | 10 | 0.001 | 0–2 | 1.3 ± 0.82 | 33 ± 20 |
| TAEEK | 10 | 1000 | 0–2 | 0.7 ± 0.82 | 18 ± 20 |
| | 10 | 500 | 0–1 | 0.3 ± 0.48 | 9 ± 13 |
| | 9 | 100 | 0–2 | 0.67 ± 0.87 | 18 ± 23 |
| | 11 | 10 | 0–1 | 0.18 ± 0.40 | 5 ± 10 |
| | 12 | 1 | 0–1 | 0.33 ± 0.49 | 8 ± 10 |
| | 10 | 0.1 | 0–0 | 0 ± 0 | 0 |
| | 10 | 0.01 | 0–0 | 0 ± 0 | 0 |
| | 10 | 0.001 | 0–0 | 0 ± 0 | 0 |

*Mean ± SD = mean ± standard deviation,
n = 10 for test and n = 80 for saline and heparin.

TABLE 3

Inhibition of Lewis Lung Tumor Neovascularization

| Group No. | Treatment | Dose (μg/kg/dose) | No. Vessels (Mean ± S.D.)* |
|---|---|---|---|
| 1 | None | 0 | 19 ± 6 |
| 2 | Cytoxan | 200 | 9 ± 5* |
| 3 | L-Glu-L-Trp | 2000 | 17 ± 7 |
| 4 | | 1000 | 12 ± 5* |
| 5 | | 500 | 9 ± 4* |
| 6 | | 250 | 7 ± 2* |
| 7 | | 125 | 6 ± 3* |

TABLE 3-continued

Inhibition of Lewis Lung Tumor Neovascularization

| Group No. | Treatment | Dose (μg/kg/dose) | No. Vessels (Mean ± S.D.)* |
|---|---|---|---|

Student-Newman-Keuls multiple pairwise comparison; statistically different than group 1 at the $p < 0.05$ level.

The results show a clear statistically significant inhibition of neovascularization as a result of treatments with either Cytoxan or L-Glu-L-Trp. Low doses of L-Glu-L-Trp were more effective in inhibiting angiogenesis (groups 4–7) than higher doses (group 3). The inverse dose-response profile, i.e., with lower activity at higher doses, is consistent with previously observed performance of other biological response modifiers in this assay (e.g., IFN-α or IL-12).

All treatments were well tolerated and no weight loss or deaths were recorded.

EXAMPLE 4

Anti-Tumor Activity of L-Glu-L-Trp: Sarcoma 180

Neovascularization is required for tumor growth. Anti-tumor activity of L-Glu-L-Trp was evaluated at an independent contract research organization. Sarcoma 180 tumors (ATCC CCL-8 CCRF S-180 II) were induced by injecting $2 \times 10^6$ cells/0.1 ml im into each rear flank of Swiss-Webster mice. Groups consisted of 10 animals (20 tumors). L-Glu-L-Trp was administered in a single 0.1 ml dose of either 10 μg/kg, 75 μg/kg, 250 μg/kg or 1000 μg/kg. Tumor size was evaluated by surgically removing and weighing the affected limbs, and comparing the weight with the weight of normal control (non-tumor) limbs. The first prophylactic drug regimen (PDR-1) consisted of 5 consecutive daily ip injections commencing on day −5 and ending of day −1. The second prophylactic drug regimen (PDR-2) consisted of 5 consecutive daily im injections to the left rear flank (tumor site) beginning on day −5 and ending on day −1. Sarcoma 180 cells were injected im on day 0. Saline 0.1 ml served as the negative control.

TABLE 4

Effect of L-Glu-L-Trp Treatments on Sarcoma 180 Tumor Size

| Group | Treatment Regimen | Dose (μg/kg) | Leg Weight (g) Left | Leg Weight (g) Right | Mean Tumor Weight[a] Left | Mean Tumor Weight[a] Right | Percent of Control Tumor Weight[b] | |
|---|---|---|---|---|---|---|---|---|
| 1A (normal) | None | 0 | 1.2 ± 0.1 | 1.2 ± 0.2 | 0 | 0 | — | — |
| 1B (tumor) | None | 0 | 3.7 ± 0.6 | 3.5 ± 0.7 | 2.5 | 2.3 | 0 | 0 |
| 2 | PDR-1 | 10 | 4.2 ± 0.9 | 4.1 ± 0.7 | 3.0 | 2.9 | 120 | 126 |
| 3 | PDR-1 | 75 | 4.2 ± 0.8 | 4.2 ± 0.8 | 3.0 | 3.0 | 120 | 130 |
| 4 | PDR-1 | 250 | 3.5 ± 1.0 | 3.1 ± 0.6 | 2.3 | 1.9 | 92 | 83 |
| 5 | PDR-1 | 1000 | 2.5 ± 0.7 | 2.2 ± 0.5 | 1.3 | 1.0 | 52 | 43 |
| 6 | PDR-2 | 10 | 3.6 ± 0.7 | 3.8 ± 0.7 | 2.4 | 2.6 | 96 | 113 |
| 7 | PDR-2 | 75 | 3.6 ± 0.7 | 3.5 ± 0.3 | 2.4 | 3.3 | 96 | 143 |
| 8 | PDR-2 | 250 | 3.0 ± 0.1 | 2.3 ± 0.5 | 1.8 | 1.1 | 72 | 48 |
| 9 | PDR-2 | 1000 | 2.4 ± 0.5 | 2.5 ± 0.5 | 1.2 | 1.3 | 48 | 57 |

[a]Mean Tumor weight = (mean leg weight treated − mean leg weight normal control);
[b]Inhibition = (tumor weight treated/tumor weight control) × 100%

The results presented in TABLE 5 show that prophylactic treatments with L-Glu-L-Trp ip or im at doses of 250 μg/kg and 1000 μg/kg inhibited subsequent im tumor growth. Interestingly, it appeared possible to invoke systemic inhibitor effects from treatments delivered at a local im site, because the im treatments delivered into the left flank inhibited subsequent tumor growth in the right flank (i.e., groups 8 and 9). The results are consistent with the inhibition of neovascularization observed in Examples 2 and 3, above.

The present invention provides a substantially novel method for inhibiting neovascularization. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method of inhibiting neovascularization in a subject in need thereof comprising:
   administering to said subject, for a time and under conditions effective to inhibit neovascularization, a pharmaceutical preparation comprising a pharmaceutically acceptable carrier and an amount of a compound effective to inhibit neovascularization with the formula of R'-Glu-Trp-R", or pharmaceutically acceptable salts thereof,
   wherein R' and/or R" is absent or
   wherein R' represents an alkyl group, an aryl group, an ester, an ether, an anhydride, or mixed alkyl/aryl derivative,
   or R', taken together with the alpha-amino group of glutamic acid, represents an amide, or an imide,
   R" represents an alkyl group, an ether, an aryl group, or mixed alkyl/aryl derivative,
   or R", taken together with the carbonyl group of tryptophan represents an imide, an ester, or an anhydride,
   wherein R' can also represent an amide bond between the amine of said Glu and the side chain carboxylate of said Glu,
   wherein neither R' nor R" contains amino acids, and
   wherein the formula weight of said compound is less than 5000 Daltons.

2. The method of claim 1, wherein the formula weight of said compound is less than 1000 Daltons.

3. The method of claim 2, wherein said compound is selected from the group consisting of: Ac-Glu-Trp, Suc-Glu-Trp, Cpr-Glu-Trp, But-Glu-Trp, and pyroGlu-Trp wherein Ac represents acetyl, Suc represents succinyl, Cpr represents cyclopropyl and But represents butyryl.

4. The method of claim 1, wherein said pharmaceutically acceptable salt is selected from the group consisting of sodium, potassium, ammonium, zinc, magnesium, and calcium.

5. The method of claim 1, wherein said pharmaceutically acceptable salt is selected from the group consisting of hydrochloride, hydrobromide, sulfate, bisulfate, acetate, oxalate, valarate, oleate, laurate, borate, benzoate, lactate, phosphate, tosylate, citrate, maleate, fumarate, succinate, and tartrate.

6. The method of claim 1, wherein the subject is afflicted with hemangioma.

7. The method of claim 1, wherein the subject is afflicted with a vascularized malignant tumor or vascularized benign tumor.

8. The method of claim 7, wherein the tumor is a tumor of the meninges, an intracerebral tumor, a sarcoma, an osteosarcoma, a tumor of the esophagus, or a tumor of the trachea.

9. The method of claim 7, wherein the tumor is a lewis carcinoma.

10. The method of claim 7, wherein the tumor is Kaposi's sarcoma.

11. The method of claim 1, comprising administering to the subject a dose of said compound of 0.5 μg per 1 kilogram body weight to 1 mg per 1 kg body weight.

12. The method of claim 11, wherein the effective amount is 1 μg/kg to 50 μg/kg body weight.

13. The method of claim 11, wherein said dose is administered daily over a period of 1 day to 30 days.

14. The method of claim 1, wherein said pharmaceutical preparation is administered intramuscularly, intranasally, transdermally, or intrabronchially.

15. The method of claim 1, wherein said pharmaceutical preparation is administered intravenously, intraperitoneally, subcutaneously, or gastrointestinally.

16. The method of claim 1, wherein said pharmaceutical preparation is an injectable solution comprising 0.001% to 0.01% of said compound.

17. The method of claim 1, wherein said pharmaceutical preparation is in a unit dose form comprising a tablet, a suppository, a capsule, an eye film, an inhalant, a mucosal spray, a nose drop, an eye drop, a toothpaste, an ointment, a water-soluble based cream, a solution, or a saline solution.

18. The method of claim 17, wherein said unit dose form consists essentially of 0.01 mg of said compound.

19. The method of claim 1, wherein the subject is not immune compromised.

20. The method of claim 1, wherein the subject is afflicted with neovascularization in post-recovery cerebrovascular accident, neovascularization due to head trauma, restenosis following angioplasty, or neovascularization due to heat or cold trauma.

21. The method of claim 1, wherein the subject is afflicted with neovascularization associated with substance-induced neovascularization of the liver, angiogenic dysfunction related to an excess of hormone, neovascular sequelae of diabetes, neovascular sequelae to hypertension, or chronic liver infection.

22. The method of claim 1, wherein the neovascular sequelae of diabetes is central serous chorioretinopathy.

23. The method of claim 1, wherein the ester is a methyl, ethyl, or other alkyl ester.

24. The method of claim 1, wherein said composition consists essentially of L-Glu-L-Trp.

25. The method of claim 1, wherein the formula weight of said compound is about 1000 Daltons.

26. A method of inhibiting neovascularization in a subject in need thereof comprising:
administering to said subject, for a time and under conditions effective to inhibit neovascularization, a pharmaceutical preparation comprising a pharmaceutically acceptable carrier and an amount of a compound effective to inhibit neovascularization with the formula of R'-Glu-Trp-R", or pharmaceutically acceptable salts thereof,
wherein R' and/or R" is absent or
wherein R' represents an alkyl group, an aryl group, an ester, an ether, an anhydride, or mixed alkyl/aryl derivative,
or R', taken together with the alpha-amino group of glutamic acid, represents an amide, or an imide,
R" represents an alkyl group, an ether, an aryl group, or mixed alkyl/aryl derivative,
or R", taken together with the carbonyl group of tryptophan represents an amide, an imide, an ester, or an anhydride,
wherein R' can also represent an amide bond between the amine of said Glu and the side chain carboxylate of said Glu,
wherein both R', taken together with the alpha-amino group of glutamic acid, and R", taken together with the carbonyl group of tryptophan, are not both amide, and
wherein the formula weight of said compound is less than 1000 Daltons.

27. The method of claim 26, wherein said pharmaceutically acceptable salt is selected from the group consisting of sodium, potassium, ammonium, zinc, magnesium, and calcium.

28. The method of claim 26, wherein said pharmaceutically acceptable salt is selected from the group consisting of hydrochloride, hydrobromide, sulfate, bisulfate, acetate, oxalate, valarate, oleate, laurate, borate, benzoate, lactate, phosphate, tosulate, citrate, maleate, fumarate, succinate, and tartrate.

29. The method of claim 26, wherein the subject is afflicted with hemangioma.

30. The method of claim 26, wherein the subject is afflicted with a vascularized malignant tumor or vascularized benign tumor.

31. The method of claim 30, wherein the tumor is a tumor of the meninges, an intracerebral tumor, a sarcoma, an osteosarcoma, a tumor of the esophagus, or a tumor of the trachea.

32. The method of claim 30, wherein the tumor is a Lewis carcinoma.

33. The method of claim 30, wherein the tumor is Kaposi's sarcoma.

34. The method of claim 26, comprising administering to the subject a dose of said compound of 0.5 $\mu$g per 1 kilogram body weight to 1 mg per 1 kg body weight.

35. The method of claim 34, wherein the effective amount is 1 $\mu$g/kg to 50 $\mu$g/kg body weight.

36. The method of claim 34, wherein said dose is administered daily over a period of 1 day to 30 days.

37. The method of claim 26, wherein said pharmaceutical preparation is administered intramuscularly, intranasally, transdermally, or intrabronchially.

38. The method of claim 26, wherein said pharmaceutical preparation is administered intravenously, intraperitoneally, subcutaneously, or gastrointestinally.

39. The method of claim 26, wherein said pharmaceutical preparation is an injectable solution comprising 0.001% to 0.01% of said compound.

40. The method of claim 26, wherein said pharmaceutical preparation is in a unit dose form comprising a tablet, a suppository, a capsule, an eye film, an inhalant, a mucosal spray, a nose drop, an eye drop, a toothpaste, an ointment, a water-soluble based cream, a solution, or a saline solution.

41. The method of claim 40, wherein said unit dose form consists essentially of 0.01 mg of said compound.

42. The method of claim 26, wherein the subject is not immune compromised.

43. The method of claim 26, wherein the subject is afflicted with neovascularization in post-recovery cerebrovascular accident, neovasuclarization due to head trauma, restenosis following angioplasty, or neovascularization due to heat or cold trauma.

44. The method of claim 26, wherein the subject is afflicted with neovascularization associated with substance-induced neovascularization of the liver, angiogenic dysfunction related to an excess of hormone, neovascular sequelae of diabetes, neovascular sequelae to hypertension, or chronic liver infection.

45. The method of claim 44, wherein the neovascular sequelae of diabetes is central serious chorioretinopathy.

46. The method of claim 26, wherein the ester is a methyl, ethyl, or other alkyl ester.

47. A method of inhibiting neovascularization in a subject in need thereof comprising:

administering to said subject, for a time and under conditions effective to inhibit neovascularization, a pharmaceutical preparation comprising a pharmaceutically acceptable carrier and an amount of a compound effective to inhibit neovascularization with the formula of R'-Glu-Trp-R", or pharmaceutically acceptable salts thereof, wherein R' and/or R" is absent or wherein R' represents an alkyl group, an aryl group, an ester, an ether, an anhydride, or mixed alkyl/aryl derivative, or R', taken together with the alpha-amino group of glutamic acid, represents an amide, or an imide, R" represents an alkyl group, an ether, an aryl group, or mixed alkyl/aryl derivative, or R", taken together with the carbonyl group of tryptophan represents an amide, an imide, an ester, or an anhydride, wherein R' can also represent an amide bond between the amine of said Glu and the side chain carboxylate of said Glu, wherein both R', taken together with the alpha-amino group of glutamic acid, and R", taken together with the carbonyl group of tryptophan, are not both amide, wherein neither R' nor R" contains amino acids, and wherein the formula weight of said compound is about 1000 Daltons.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 4 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 1:

Glu Trp Glu Trp
1

(2) INFORMATION FOR SEQ ID NO: 2:

(i) SEQUENCE CHARACTERISTICS:
       (A) LENGTH: 5 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 2:

Glu Trp Lys His Gly
1               5

(2) INFORMATION FOR SEQ ID NO: 3:

(i) SEQUENCE CHARACTERISTICS:
       (A) LENGTH: 6 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 3:

Glu Trp Lys Lys His Gly
1               5

(2) INFORMATION FOR SEQ ID NO: 4:

(i) SEQUENCE CHARACTERISTICS:
       (A) LENGTH: 5 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 4:

Arg Lys Glu Trp Tyr
1               5

(2) INFORMATION FOR SEQ ID NO: 5:

(i) SEQUENCE CHARACTERISTICS:
       (A) LENGTH: 4 amino acids
       (B) TYPE: amino acid
       (C) STRANDEDNESS: <Unknown>
       (D) TOPOLOGY: linear

```
        (ii) MOLECULE TYPE: peptide (xi) SEQUENCE DESCRIPTION: SEQ ID NO: 5:

Arg Lys Glu Trp
1

(2) INFORMATION FOR SEQ ID NO: 6:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 6:

Lys Glu Trp Tyr
1

(2) INFORMATION FOR SEQ ID NO: 7:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 7:

Thr Ala Glu Glu Lys
1               5
```